US008679010B2

(12) United States Patent
Doerr et al.

(10) Patent No.: US 8,679,010 B2
(45) Date of Patent: Mar. 25, 2014

(54) IMPLANTABLE SENSOR DEVICE

(75) Inventors: Thomas Doerr, Berlin (DE); Marc Hauer, Zurich (CH)

(73) Assignee: Dyconex AG, Bassersdorf (CH)

( * ) Notice: Subject to any disclaimer, the term of this patent is extended or adjusted under 35 U.S.C. 154(b) by 191 days.

(21) Appl. No.: 13/169,450

(22) Filed: Jun. 27, 2011

(65) Prior Publication Data

US 2012/0016212 A1 Jan. 19, 2012

Related U.S. Application Data

(60) Provisional application No. 61/364,814, filed on Jul. 16, 2010.

(51) Int. Cl.
*A61B 5/00* (2006.01)
*G06F 19/00* (2011.01)

(52) U.S. Cl.
CPC ........ *G06F 19/3406* (2013.01); *G06F 19/3412* (2013.01)
USPC ......................................................... 600/300

(58) Field of Classification Search
USPC ........... 600/300–301, 485, 486, 488; 417/417
See application file for complete search history.

(56) References Cited

U.S. PATENT DOCUMENTS

| | | | |
|---|---|---|---|
| 6,524,256 B2* | 2/2003 | Schaldach et al. | 600/486 |
| 6,877,835 B2* | 4/2005 | Kato et al. | 347/30 |
| 8,083,707 B2* | 12/2011 | Tosaya et al. | 604/22 |
| 8,162,924 B2* | 4/2012 | Boyden et al. | 604/890.1 |
| 8,221,097 B2* | 7/2012 | Gray | 417/417 |
| 2002/0115986 A1* | 8/2002 | Shadduck | 604/891.1 |
| 2003/0125613 A1* | 7/2003 | Enegren et al. | 600/347 |
| 2004/0230117 A1* | 11/2004 | Tosaya et al. | 600/439 |
| 2007/0066873 A1* | 3/2007 | Kamath et al. | 600/300 |
| 2010/0232992 A1* | 9/2010 | Gray | 417/417 |

* cited by examiner

*Primary Examiner* — Bill Thomson
*Assistant Examiner* — Bobby Soriano
(74) *Attorney, Agent, or Firm* — Buchanan Ingersoll & Rooney PC

(57) ABSTRACT

An implantable sensor device for capturing at least one physical, chemical, biological or physiological parameter in the body of a living being wearing the sensor device upon contact with the body fluid or tissue of the same, including a sensor housing, a sensor element that is accommodated in the sensor housing and has a capturing section, which has direct contact with the body fluid or the body tissue, or which internally adjoins a surface or opening section of the sensor housing that has contact with the body fluid or the body tissue, and a mechanically acting sensor cleaning device for cleaning the capturing section of the sensor element and/or the surface or opening section of the sensor housing adjoining the same.

8 Claims, 8 Drawing Sheets

IMPLANTABLE SENSOR DEVICE

CROSS-REFERENCE TO RELATED APPLICATIONS

This patent application claims the benefit of co-pending U.S. Provisional Patent Application No. 61/364,814, filed on Jul. 16, 2010, which is hereby incorporated by reference in its entirety.

TECHNICAL FIELD

The invention relates to an implantable sensor device for capturing at least one physical, chemical, biological or physiological parameter in the body of a living being wearing the sensor device upon contact with the body medium, which means, in the context of the invention, body fluid or tissue of the same.

BACKGROUND

Such sensor devices have been known for quite some time in a variety of designs primarily as signal transmitters for medical electronic devices, which are likewise implanted, but also as signal transmitters for external patient monitoring and have been used clinically. Particularly common are sensing electrodes for tapping electric potential in the body, such as heart or other muscle action potential or cerebral activity. However, non-electric sensors, such as optical sensors for capturing the blood oxygen saturation, pressure sensors for capturing the blood and internal vessel pressure, electrochemical sensors and the like, are also known and used at least selectively.

Particularly in the case of non-electric sensor types, during permanent use, frequently the problem has arisen that the sensor surface becomes overgrown with endogenous tissue or that denatured proteins from the surrounding body fluid deposit on the sensor surface. As a result, at least the sensitivity of the sensor is disadvantageously diminished, and frequently the functional capability is completely lost and the sensor becomes unusable.

As a counter-measure, a variety of coatings for the sensor surfaces have been developed, which are designed to destroy the biochemical deposition chain. Furthermore, the approach of "burning off" the capturing surfaces of sensor arrays designed specifically with respect to the cleaning function has been pursued. These approaches have proven to be only conditionally successful.

The invention is directed at overcoming one or more of the above-identified problems.

SUMMARY OF THE INVENTION

It is therefore the object of the invention to provide an improved sensor device of the type stated above, which in permanent operation has improved reliability and a longer service life.

This object is achieved by a sensor device having the characteristics of the independent claim(s). Advantageous refinements of the inventive concept are the subject matter of the dependent claims.

The invention proposes to provide a mechanically acting sensor cleaning device in the sensor device for cleaning the capturing section of the sensor element and/or the surface section of the sensor housing adjoining the same.

In one embodiment of the invention, the sensor cleaning device comprises gas bubble generation means, which are designed and disposed such that gas bubbles are generated in the capturing section of the sensor element or the surface section of the sensor housing adjoining the same or are moved over the same.

This embodiment can be refined in a variety of ways. In one embodiment, electrothermally acting gas bubble generation means are provided, which comprise, in particular, a cleaning current generation device and a conductor means connected thereto. "Conductor means" means, in the context of the invention, a conductor assembly or a conductive layer. According to a further embodiment, the gas bubble generation means comprise an ultrasonic generator, particularly a piezo oscillator that is connected to an ultrasonic generator.

In a further embodiment, electrochemically acting gas bubble generation means are provided, which, in particular, comprise at least one electrode and counter-electrode and a cleaning current generation device connected to the same. An embodiment of the gas bubble generation means has a similar design, wherein the gas bubble generation means are designed to bring about a high-voltage flashover, or sparkover, and comprise, in particular, at least one electrode and counter-electrode and a cleaning voltage generation device connected to the same.

Both the electrochemically acting and the high-voltage gas bubble generation devices can advantageously be used in a further embodiment. In this embodiment, the capturing section and at least one of the electrodes are disposed in a lumen of the sensor housing having an opening such that the gas formation caused by an electrochemical reaction or the high-voltage flashover generates a pressure wave in the lumen, which propagates through the opening.

With respect to the avoidance of physiological problems during the operation of the sensor cleaning device, in a further embodiment the gas bubble generation means are designed such that they generate gas bubbles having an average volume of less than 1 ml per cleaning cycle or per day. Therefore, the maximum cleaning time shall be limited per cleaning cycle and/or per day to ensure a maximum gas bubble volume of 1 ml considering cleaning surface and parameters (voltage, current, etc.).

According to a further embodiment, the sensor cleaning device comprises time control means for the time-dependent, in particular, periodic, activation of the cleaning function. As a result, the energy consumption (which usually places strain on the battery of the sensor device) of the cleaning processes can be minimized when taking empirical values into account with respect to the growth time duration of blood and/or tissue elements. In an alternative variant, or a variant that can be combined with the above embodiment, the sensor cleaning device comprises sensor signal-dependent control means for activating the cleaning function in response to an abnormal time dependence of the signals of the sensor element. While this latter version requires a higher implementation complexity, it allows even better adaptation of the cleaning function to the actual deposition of the sensor surface during the operation of the sensor device.

Various other objects, aspects and advantages of the invention can be obtained from a study of the specification, the drawings, and the appended claims.

DESCRIPTION OF THE DRAWINGS

Advantages and functional characteristics of the invention will additionally become apparent hereinafter from the description of exemplary embodiments based on the figures. Shown are.

DETAILED DESCRIPTION

Figure 1A:
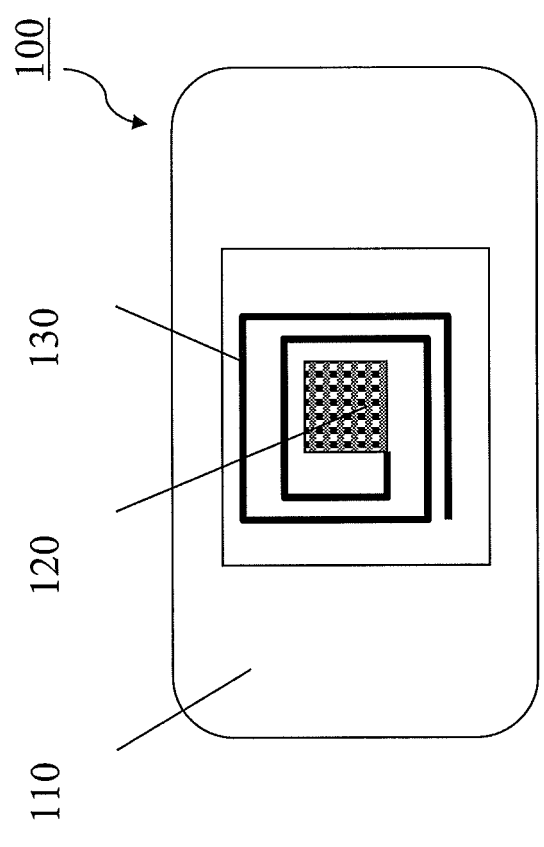
FIGS. 1A and 1B are schematic illustrations of a passive sensor implant.
Figure 1B:
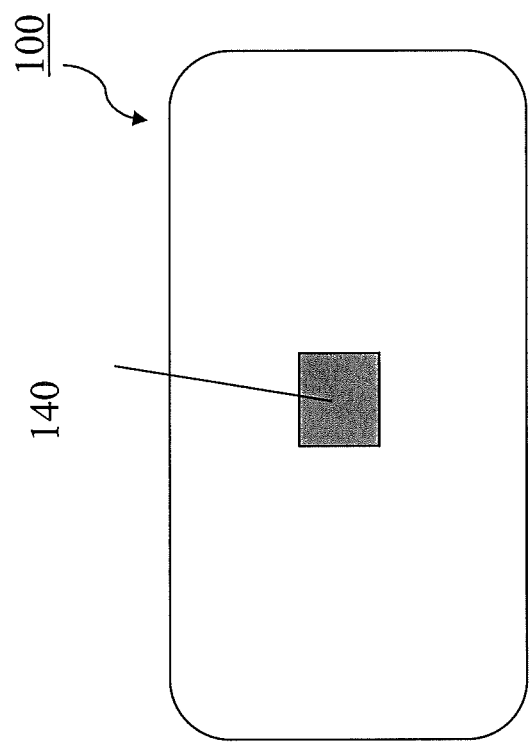

FIGS. 1A and 1B show schematic top views of the basic design of a passive sensor implant or an implantable sensor device 100, comprising a sensor housing 110, a sensor element 120, and a coil 130 for signal transmission in connection with a telemetric activation of the sensor and communication with a telemetry device located outside of the body of a wearer (not shown). FIG. 1B shows that the sensor is hermetically enclosed by the sensor housing 110 in the usage state, wherein only a sensor window or a capturing section 140 that is required for obtaining the sensor information upon contact with the body fluid or body tissue of the wearer is not encapsulated.

Figure 2:
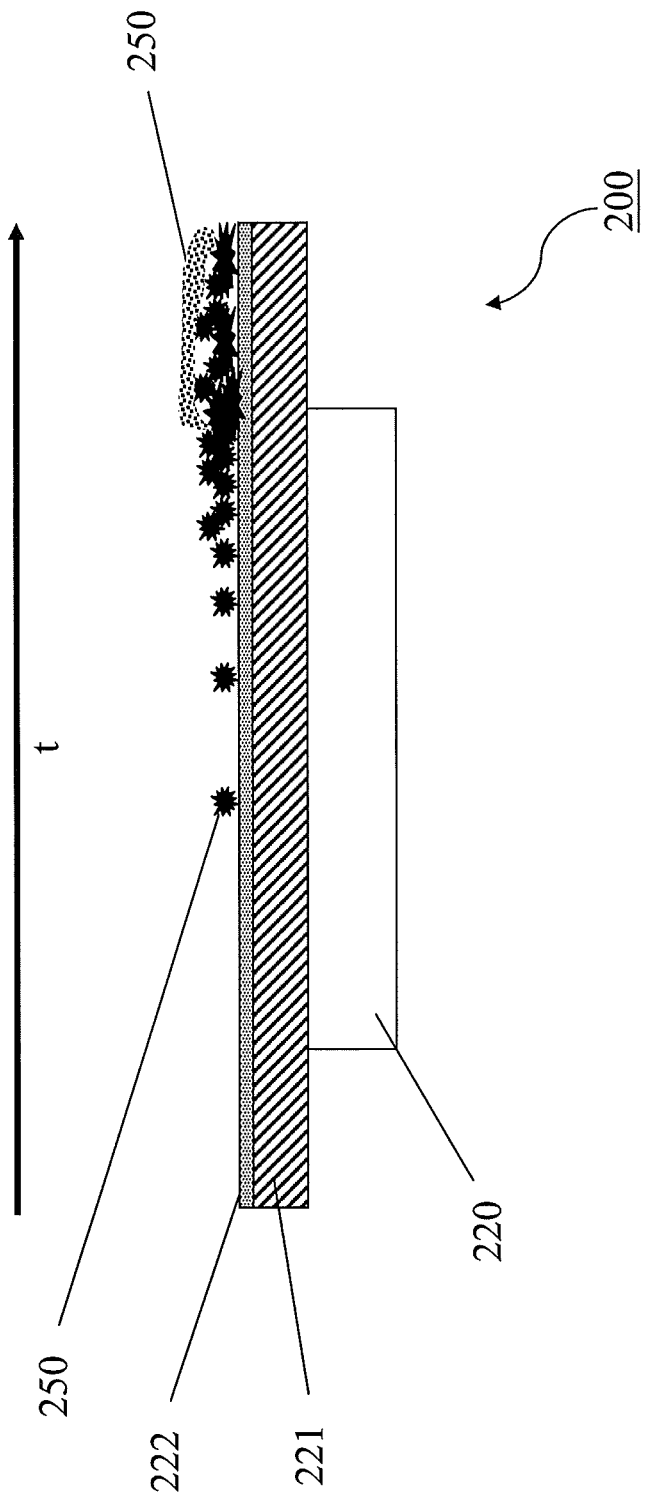
FIG. 2 is a synoptic illustration to highlight the object to be achieved by the invention.

FIG. 2 illustrates the problem which arises during long-term use with such implantable sensor devices in the body of a wearer, and which has prompted the deliberations of the inventors. A sensor element illustrated here as a "black box" and denoted with numeral 220 is covered by a protective layer 221, which is transparent to the sensor information and which, in turn, has a special surface layer 222 that inhibits the growth of biological material. However, over the course of time—symbolized here with a time axis "t"—the endogenous proteins also degenerate on this special surface 222 and result in deposits 250, which increasingly encapsulate the sensor element 220 with respect to the body fluids containing the sensor information, thereby rendering it unusable.

Figure 3:
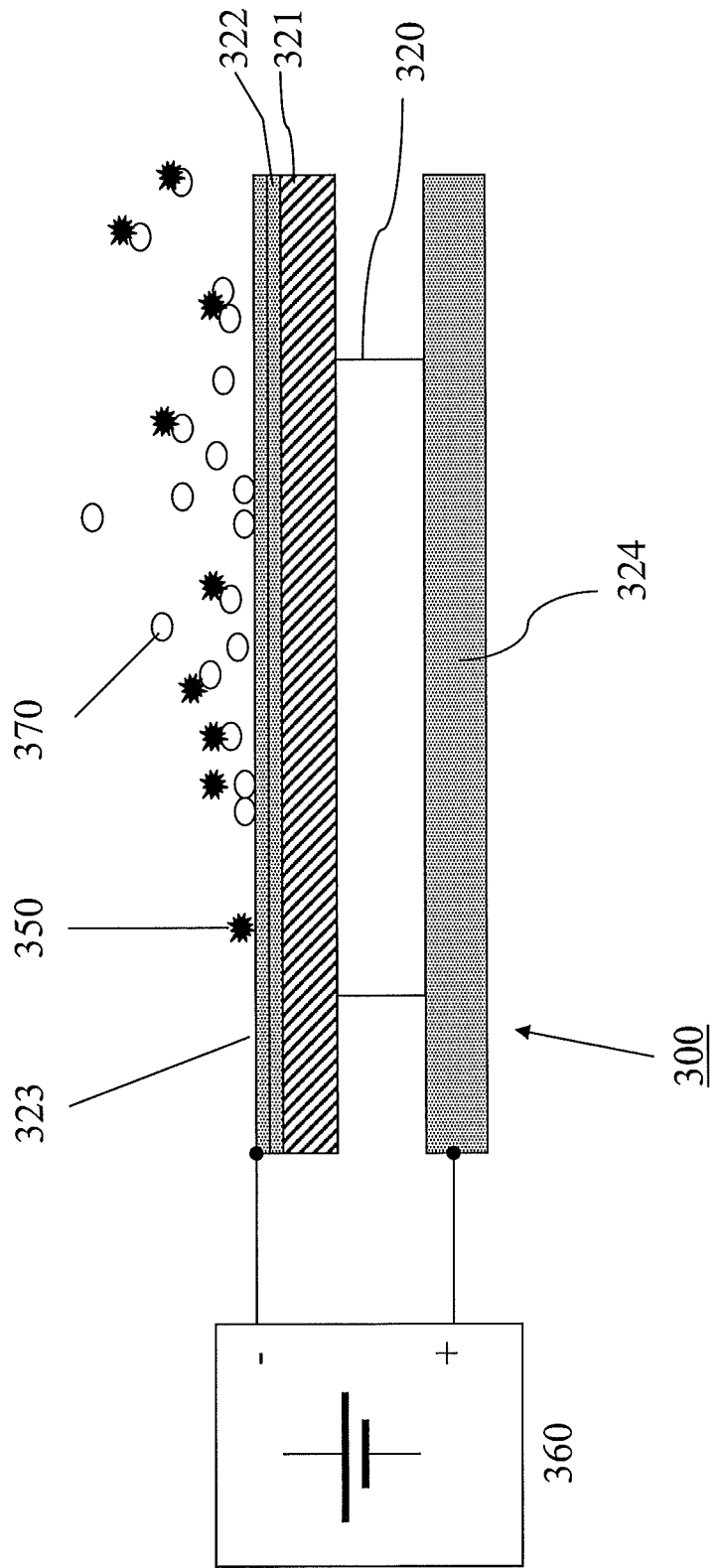
FIG. 3 is a schematic illustration of one embodiment of the invention.

In a similar illustration as in FIG. 2, FIG. 3 shows the basic design of a first sensor device 300 according to the invention, comprising a sensor element 320, which additionally has an electrically conductive surface 323 over the transparent protective layer 321 and the growth-inhibiting surface layer 332, and which is likewise transparent to the sensor information. An electric potential is applied at periodic intervals to the surface (the capturing section) of the sensor device by way of a counter-electrode 324 provided at the back of the sensor element 320 and a controllable power source 360. In coordination with the electric parameters of the electrode layers 322, 324 and the body fluids typically surrounding the sensor device, this voltage is selected such that a current flows to the capturing surface which is sufficient to bring about an electrochemical reaction and the development of gas bubbles 370.

During the periodic cleaning processes, the gas bubbles 370 detach degenerated proteins 350, that have meanwhile deposited, from the capturing surface. The duration and intensity of the current input is defined such that a short-term bubble formation takes place over the entire capturing surface, however, the surrounding body tissue is not damaged and the gas volume that is generated is physiologically safe.

Figure 4:
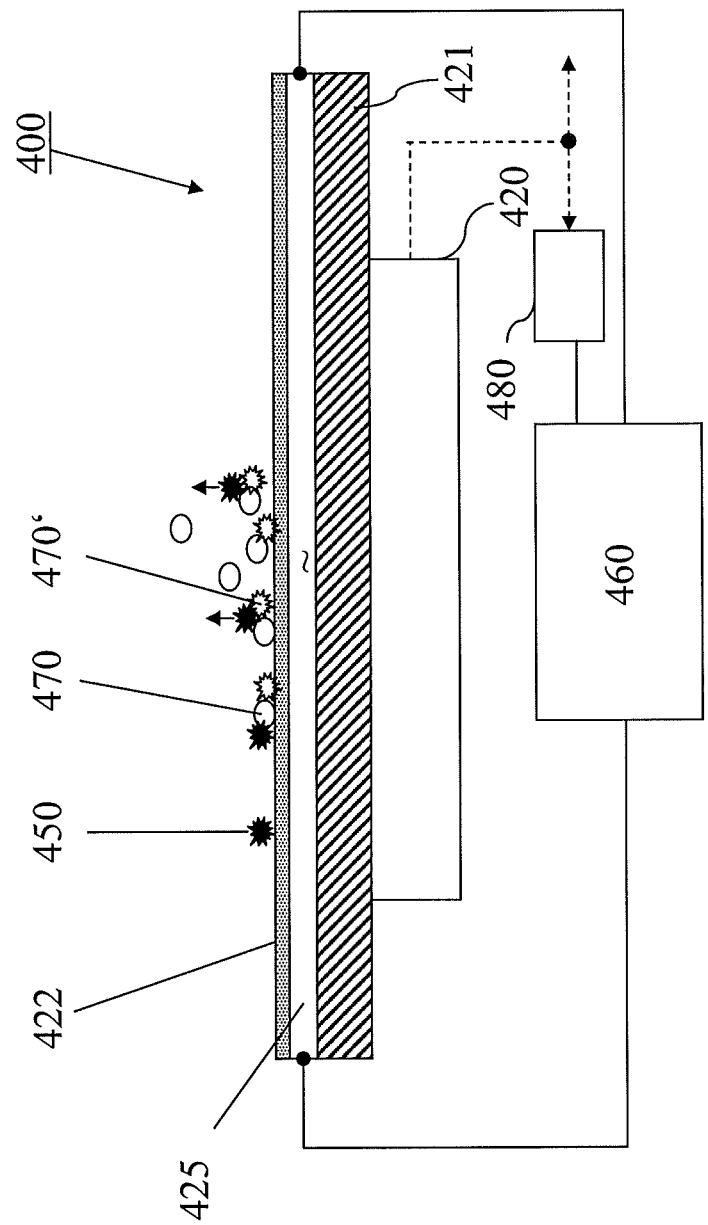
FIG. 4 is a schematic illustration of a further embodiment of the invention.

As a further embodiment of the invention, FIG. 4 shows a sensor device 400 which again comprises a sensor element 420 and the usual transparent protective layer 421, however, in which gas bubble generation means that function differently than in the first embodiment are provided.

In this case, these means comprise a piezo oscillator 425, which is periodically excited by an ultrasonic generator 460 to oscillate in the ultrasonic range so as to perform a cleaning cycle. The piezo oscillator 425 is disposed on the surface of the conventional transparent protective layer 421, and the growth-inhibiting surface coating 422 is disposed on the piezo oscillator 425 in this case. The ultrasonic vibrations generate small gas bubbles 470 on the sensor surface, which collapse directly after they have been produced (see reference numeral 470') and, in the process, detach proteins 450, that have meanwhile deposited, from the capturing surface. The mechanism of action of this embodiment of the invention corresponds at least partially to that of an ultrasonic cleaning bath.

In the ultrasonic generator, a control device 480 is provided as a control device for controlling the cleaning procedures, which in the simplest case can be designed as a timer, but in a more intelligent embodiment (illustrated with dotted lines) can be connected on the input side to the sensor element 420 and capture a degeneration of the sensor signal, using it as a trigger to start a cleaning process.

Figure 5:
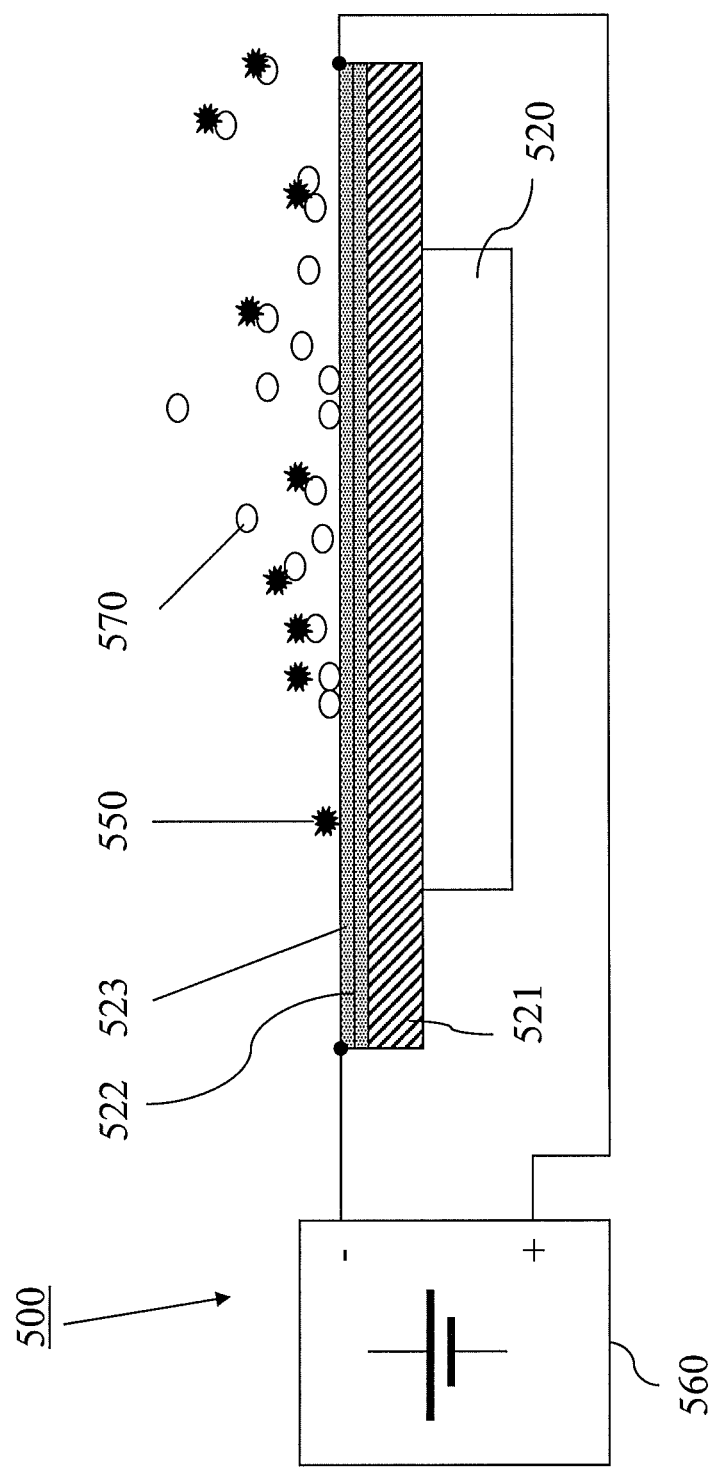
FIG. 5 is a schematic illustration of a further embodiment of the invention.

FIG. 5 shows a variant of the invention that is very similar to the embodiment of FIG. 2, wherein, in terms of the design, basically the counter-electrode has been eliminated. The remaining parts correspond to the embodiment of FIG. 3 and are therefore denoted with similar reference numerals. The surface layer 523 is a conductive layer which is transparent to the sensor signal and which, when a briefly applied, relatively high current passes through, heats up so strongly that gas bubbles 570 form in the surrounding body fluid.

Figure 6:
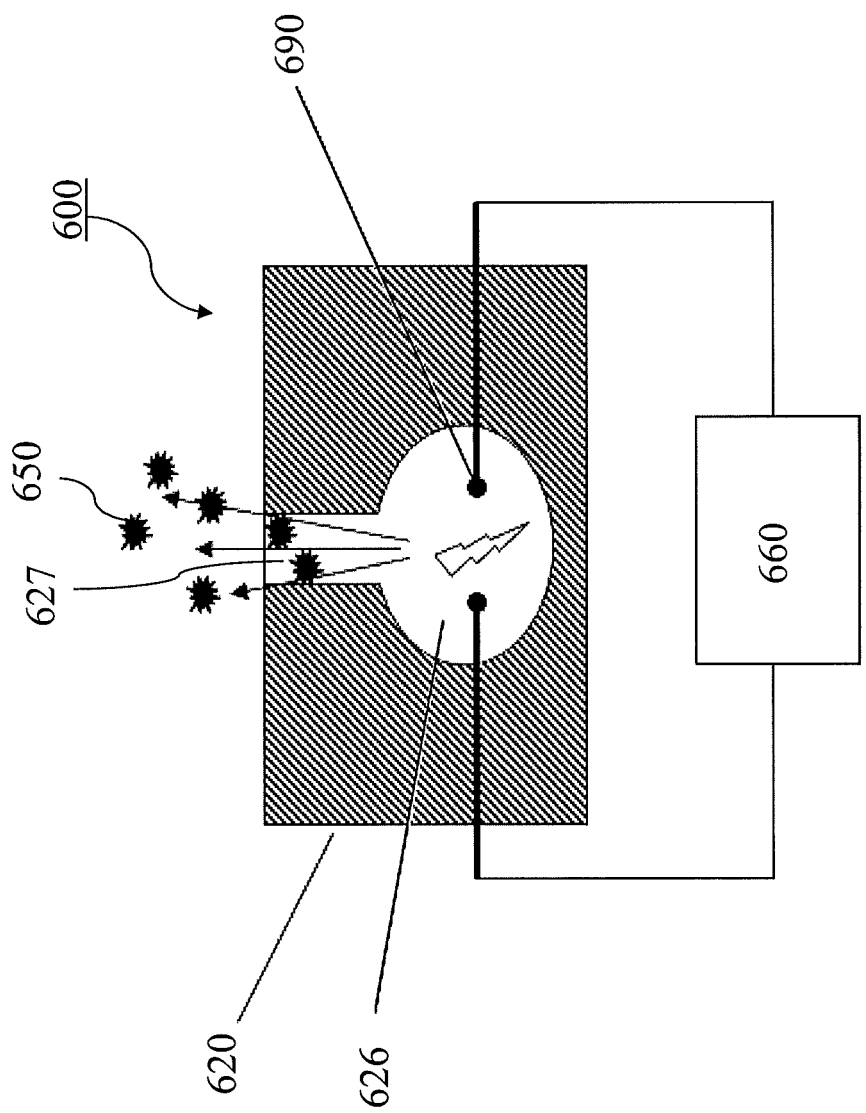
FIG. 6 is a schematic illustration of a further embodiment of the invention.

The further sensor device 600 according to FIG. 6 has a different mechanism of action. The sensor element 620 thereof has a lumen 626, in which a capturing section (which is not denoted separately here) of the sensor element is located, comprising an opening 627, through which the lumen is in fluid connection with the surrounding body fluids of the implant wearer. In order to clean this opening on a regular basis, two electrodes 690 are disposed in the lumen 626, which are connected to a high-voltage generator 660 and are supplied by the same periodically with high voltage for the cleaning cycles. The resulting explosive gas formation generates a considerable overpressure in the lumen 626, as a result of which denatured proteins 650 clogging the opening 627 are expelled. In this way, the opening of the sensor element 620 is cleaned reliably.

Figure 7:
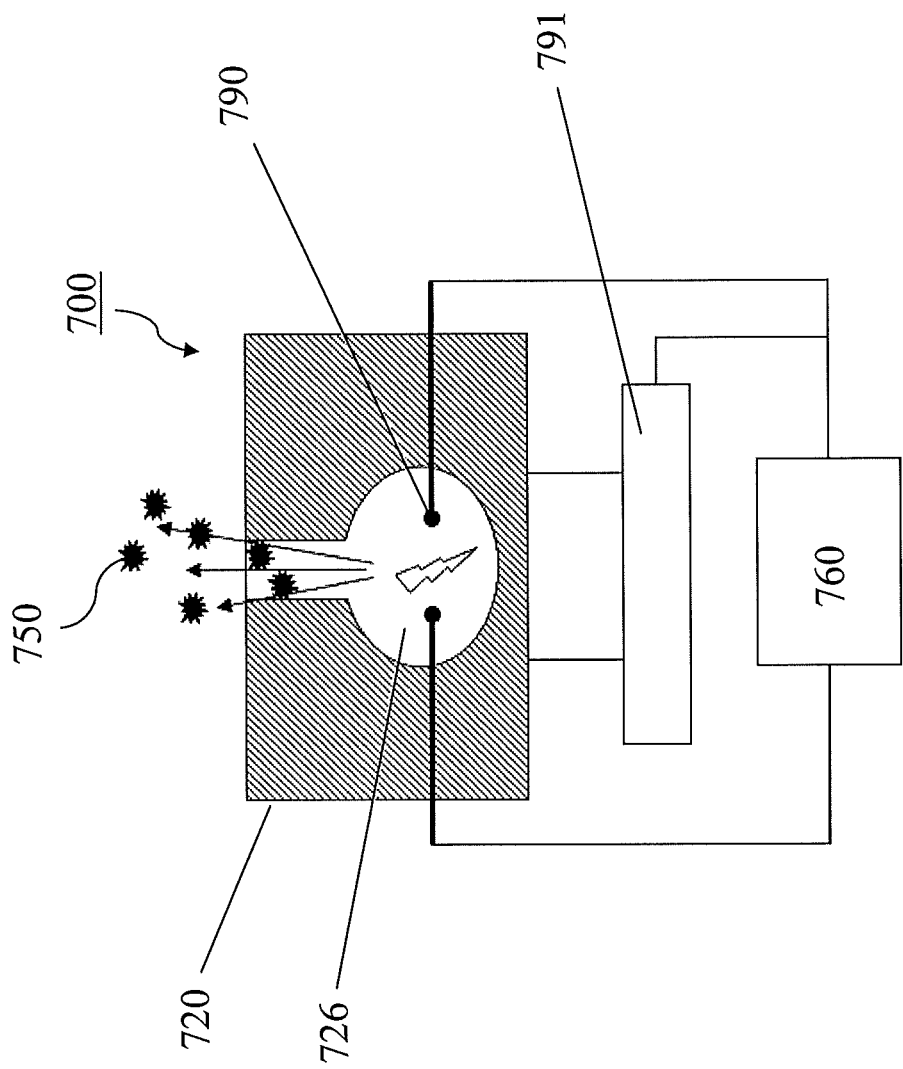
FIG. 7 is a schematic illustration of a further embodiment of the invention.

As a modified embodiment of the embodiment described last, FIG. 7 shows a sensor device 700 which has substantially the same design as the sensor device 600 according to FIG. 6, however, where a different cleaning mechanism is employed. The gases in the lumen 726 here are generated by an electrochemical gas formation on one of the two electrodes 790. The other of the two electrodes can form the required counter-electrode, however, it is also possible—as is shown additionally synoptically in the figure—that a counter-electrode 791 is provided which is located outside of the lumen 726.

The implementation of the invention is not limited to the concepts highlighted above and the examples that are described, but is likewise possible in a plurality of modifications, which are within the scope of standard practice in the art.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. An implantable sensor device for capturing at least one physical, chemical, biological or physiological parameter in a body of a living being wearing the sensor device upon contact with the body medium of the same, the sensor device comprising:
   a sensor housing;
   a sensor element that is accommodated in the sensor housing and has a capturing section, which has direct contact with the body medium; and
   a mechanically acting sensor cleaning device for cleaning the capturing section of the sensor element,
   wherein the sensor cleaning device comprises gas bubble generation means, which are designed and disposed such that gas bubbles are generated in the capturing section of the sensor element, and
   wherein the gas bubble generation means comprise electrothermally acting gas bubble generation means, which comprise a cleaning current generation device and a conductor means connected thereto.

2. The sensor device according to claim 1, wherein the gas bubble generation means are designed such that they generate gas bubbles having an average volume of less than 1 ml.

3. The sensor device according to claim 1, wherein the sensor cleaning device comprises time control means for time-dependent, periodic activation of the cleaning function.

4. The sensor device according to claim 1, wherein the sensor cleaning device comprises sensor signal-dependent control means for activating the cleaning function in response to an abnormal time dependence of the signals of the sensor element.

5. An implantable sensor device for capturing at least one physical, chemical, biological or physiological parameter in a body of a living being wearing the sensor device upon contact with the body medium of the same, the sensor device comprising:
   a sensor housing;
   a sensor element that is accommodated in the sensor housing and has a capturing section, which internally adjoins a surface or opening section of the sensor housing that has contact with the body medium; and
   a mechanically acting sensor cleaning device for cleaning the surface or opening section of the sensor housing adjoining the same,
   wherein the sensor cleaning device comprises gas bubble generation means, which are designed and disposed such that gas bubbles are generated in the surface or opening section of the sensor housing adjoining the same or are moved over the capturing section of the sensor element, and
   wherein the gas bubble generation means comprise electrothermally acting gas bubble generation means, which comprise a cleaning current generation device and a conductor means connected thereto.

6. The sensor device according to claim 5, wherein the gas bubble generation means are designed such that they generate gas bubbles having an average volume of less than 1 ml.

7. The sensor device according to claim 5, wherein the sensor cleaning device comprises time control means for time-dependent, periodic activation of the cleaning function.

8. The sensor device according to claim 5, wherein the sensor cleaning device comprises sensor signal-dependent control means for activating the cleaning function in response to an abnormal time dependence of the signals of the sensor element.

* * * * *